(12) United States Patent
Manoj et al.

(10) Patent No.: US 8,575,322 B2
(45) Date of Patent: Nov. 5, 2013

(54) POLYNUCLEOTIDE AND POLYPEPTIDE SEQUENCE AND METHODS THEREOF

(75) Inventors: Mulakkapurath Narayanan Manoj, Bangalore Karnataka (IN); Venkata Ramachandra Rao Vasamsetty, Bangalore Karnataka (IN); Madhuri Baliga, Bangalore Karnataka (IN); Kirubakaran Naveen Kumar, Bangalore Karnataka (IN); Chandrasekhar Bhaskaran Nair, Bangalore Karnataka (IN); Pillarisetti Venkata Subbarao, Bangalore Karnataka (IN)

(73) Assignee: Bigtec Private Limited, Malleshwaram Bangalore Karnataka (IN)

( * ) Notice: Subject to any disclaimer, the term of this patent is extended or adjusted under 35 U.S.C. 154(b) by 0 days.

(21) Appl. No.: 13/256,028

(22) PCT Filed: Mar. 12, 2010

(86) PCT No.: PCT/IN2010/000144
§ 371 (c)(1),
(2), (4) Date: Nov. 28, 2011

(87) PCT Pub. No.: WO2010/103546
PCT Pub. Date: Sep. 16, 2010

(65) Prior Publication Data
US 2012/0077966 A1    Mar. 29, 2012

(30) Foreign Application Priority Data

Mar. 12, 2009  (IN) .............................. 567/CHE/2009

(51) Int. Cl.
*C07H 21/04* (2006.01)
*C12N 15/17* (2006.01)

(52) U.S. Cl.
USPC ...... 536/23.5; 435/320.1; 435/69.1; 435/69.9

(58) Field of Classification Search
None
See application file for complete search history.

(56) References Cited

U.S. PATENT DOCUMENTS

2004/0067874 A1    4/2004 Markussen et al.

OTHER PUBLICATIONS

G. Zhong, et al.; "Pilot-scale production and purification of staphylokinase-based fusion protein over-expressed in *Escherichia coli*"; Frontiers in Biology China; Feb. 2009, vol. 4, No. 1; pp. 75-81 (10 pages).
International Search Report and Written Opinion issued in correspongind PCT Application No. PCT/IN2010/000144 dated Nov. 9, 2010 (12 pages).
International Preliminary Report on Patentability issued in corresponding PCT Application No. PCT/IN2010/000144 dated Jan. 11, 2011 (8 pages).
"Purification and Characterization of Papaya Glutamine Cyclotransferase, a Plant Enzyme Highly Resistant to Chemical, Acid, and Thermal Denaturation"; Samira Zerhouni et al.; Elsevier Science B.V.; 1998; pp. 275-290.

*Primary Examiner* — Gyan Chandra
(74) *Attorney, Agent, or Firm* — Osha • Liang LLP

(57) ABSTRACT

The present disclosure relates to a field of recombinant DNA therapeutics. It involves the bio-informatics design, synthesis of artificial gene for human insulin precursor including leader peptide coding sequence, cloning in an expression vector and expression in an organism, preferably *Pichia pastoris*. The present disclosure also relates to methods of downstream processing for obtaining protein precursor molecules and subsequent conversion of precursor molecules to functional proteins.

18 Claims, 10 Drawing Sheets

Assembly PCR 2

1 - 100 bp DNA Marker

2 - Tube 1

3 - Tube 2

4 - Tube 3

5 - Tube 4

Figure 15

SEQUENCE LISTING

```
<160> NUMBER OF SEQ ID NOS: 28

<210> SEQ ID NO 1
<211> LENGTH: 138
<212> TYPE: PRT
<213> ORGANISM: Artificial Sequence
<220> FEATURE:
<223> OTHER INFORMATION: Insulin precursor-secretion signal fusion
      protein

<400> SEQUENCE: 1

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg Phe Val Asn Gln His Leu Cys Gly Ser His Leu
                85                  90                  95
```

Val Glu Ala Leu Tyr Leu Val Cys Gly Glu Arg Gly Phe Phe Tyr Thr
            100                 105                 110

Pro Lys Ala Ala Lys Gly Ile Val Glu Gln Cys Cys Thr Ser Ile Cys
        115                 120                 125

Ser Leu Tyr Gln Leu Glu Asn Tyr Cys Asn
    130                 135

<210> SEQ ID NO 2
<211> LENGTH: 417
<212> TYPE: DNA
<213> ORGANISM: Artificial Sequence
<220> FEATURE:
<223> OTHER INFORMATION: Insulin precursor-secretion signal fusion
      protein gene

<400> SEQUENCE: 2
atgagatttc catctatttt cactgctgtt ttgtttgctg cttcttctgc tttggctgct      60
ccagttaaca ccactactga agatgaaact gctcagattc agctgaagc tgttattggt     120 tactctgatt tggaaggtga ttttgatgtt gctgttttgc catttctaa ctctaccaac     180 aatggtttgt tgtttatcaa cactactatt gcttctattg ctgctaagga agaaggtgtt    240
tctttggaga agagatttgt taaccaacac ttgtgcggtt ctcacttggt tgaagctttg    300
tacttggttt gtggtgaaag aggttttttc tacactccaa aggctgccaa gggtattgtt    360
gaacaatgtt gcacttcaat ctgttctttg taccaattgg agaactactg taactaa       417

<210> SEQ ID NO 3
<211> LENGTH: 44
<212> TYPE: DNA
<213> ORGANISM: Artificial Sequence
<220> FEATURE:
<223> OTHER INFORMATION: Synthetic oligonucleotide (F0)

<400> SEQUENCE: 3
gactggttcc aattgacaag cggatccaaa cgatgagatt tcca                      44

<210> SEQ ID NO 4
<211> LENGTH: 26
<212> TYPE: DNA
<213> ORGANISM: Artificial Sequence
<220> FEATURE:
<223> OTHER INFORMATION: Synthetic oligonucleotide (R0)

<400> SEQUENCE: 4
gatccgcttg tcaattggaa ccagtc                                          26

<210> SEQ ID NO 5
<211> LENGTH: 37
<212> TYPE: DNA
<213> ORGANISM: Artificial Sequence
<220> FEATURE:
<223> OTHER INFORMATION: Synthetic oligonucleotide (R19)

<400> SEQUENCE: 5
aaacagcagt gaaaatagat ggaaatctca tcgtttg                              37

<210> SEQ ID NO 6
<211> LENGTH: 36
<212> TYPE: DNA
<213> ORGANISM: Artificial Sequence
<220> FEATURE:
<223> OTHER INFORMATION: Synthetic oligonucleotide (F37)

<400> SEQUENCE: 6

-continued tctattttca ctgctgtttt gtttgctgct tcttct         36

<210> SEQ ID NO 7
<211> LENGTH: 33
<212> TYPE: DNA
<213> ORGANISM: Artificial Sequence
<220> FEATURE:
<223> OTHER INFORMATION: Synthetic oligonucleotide (R56)

<400> SEQUENCE: 7
ctggagcagc caaagcagaa gaagcagcaa aca         33

<210> SEQ ID NO 8
<211> LENGTH: 35
<212> TYPE: DNA
<213> ORGANISM: Artificial Sequence
<220> FEATURE:
<223> OTHER INFORMATION: Synthetic oligonucleotide (F73)

<400> SEQUENCE: 8
gctttggctg ctccagttaa caccactact gaaga         35

<210> SEQ ID NO 9
<211> LENGTH: 37
<212> TYPE: DNA
<213> ORGANISM: Artificial Sequence
<220> FEATURE:
<223> OTHER INFORMATION: Synthetic oligonucleotide (R89)

<400> SEQUENCE: 9
ggaatctgag cagtttcatc ttcagtagtg gtgttaa         37

<210> SEQ ID NO 10
<211> LENGTH: 36
<212> TYPE: DNA
<213> ORGANISM: Artificial Sequence
<220> FEATURE:
<223> OTHER INFORMATION: Synthetic oligonucleotide (F108)

<400> SEQUENCE: 10
tgaaactgct cagattccag ctgaagctgt tattgg         36

<210> SEQ ID NO 11
<211> LENGTH: 37
<212> TYPE: DNA
<213> ORGANISM: Artificial Sequence
<220> FEATURE:
<223> OTHER INFORMATION: Synthetic oligonucleotide (R126)

<400> SEQUENCE: 11
accttccaaa tcagagtaac caataacagc ttcagct         37

<210> SEQ ID NO 12
<211> LENGTH: 38
<212> TYPE: DNA
<213> ORGANISM: Artificial Sequence
<220> FEATURE:
<223> OTHER INFORMATION: Synthetic oligonucleotide (F144)

<400> SEQUENCE: 12
ttactctgat ttggaaggtg attttgatgt tgctgttt         38

<210> SEQ ID NO 13
<211> LENGTH: 39
<212> TYPE: DNA
<213> ORGANISM: Artificial Sequence

```
<220> FEATURE:
<223> OTHER INFORMATION: Synthetic oligonucleotide (R163)

<400> SEQUENCE: 13
ggtagagtta gaaatggca aaacagcaac atcaaaatc                              39

<210> SEQ ID NO 14
<211> LENGTH: 41
<212> TYPE: DNA
<213> ORGANISM: Artificial Sequence
<220> FEATURE:
<223> OTHER INFORMATION: Synthetic oligonucleotide (F182)

<400> SEQUENCE: 14
tgccattttc taactctacc aacaatggtt tgttgtttat c                          41

<210> SEQ ID NO 15
<211> LENGTH: 42
<212> TYPE: DNA
<213> ORGANISM: Artificial Sequence
<220> FEATURE:
<223> OTHER INFORMATION: Synthetic oligonucleotide (R202)

<400> SEQUENCE: 15
aatagaagca atagtagtgt tgataaacaa caaaccattg tt                         42

<210> SEQ ID NO 16
<211> LENGTH: 38
<212> TYPE: DNA
<213> ORGANISM: Artificial Sequence
<220> FEATURE:
<223> OTHER INFORMATION: Synthetic oligonucleotide (F223)

<400> SEQUENCE: 16
aacactacta ttgcttctat tgctgctaag gaagaagg                              38

<210> SEQ ID NO 17
<211> LENGTH: 36
<212> TYPE: DNA
<213> ORGANISM: Artificial Sequence
<220> FEATURE:
<223> OTHER INFORMATION: Synthetic oligonucleotide (R244)

<400> SEQUENCE: 17
tctcttctcc aaagaaacac cttcttcctt agcagc                                36

<210> SEQ ID NO 18
<211> LENGTH: 38
<212> TYPE: DNA
<213> ORGANISM: Artificial Sequence
<220> FEATURE:
<223> OTHER INFORMATION: Synthetic oligonucleotide (F261)

<400> SEQUENCE: 18
tgtttctttg gagaagagat tgttaacca acacttgt                               38

<210> SEQ ID NO 19
<211> LENGTH: 36
<212> TYPE: DNA
<213> ORGANISM: Artificial Sequence
<220> FEATURE:
<223> OTHER INFORMATION: Synthetic oligonucleotide (R280)

<400> SEQUENCE: 19
aaccaagtga gaaccgcaca agtgttggtt aacaaa                                36
```

```
<210> SEQ ID NO 20
<211> LENGTH: 36
<212> TYPE: DNA
<213> ORGANISM: Artificial Sequence
<220> FEATURE:
<223> OTHER INFORMATION: Synthetic oligonucleotide (F299)

<400> SEQUENCE: 20
gcggttctca cttggttgaa gctttgtact tggttt                              36

<210> SEQ ID NO 21
<211> LENGTH: 38
<212> TYPE: DNA
<213> ORGANISM: Artificial Sequence
<220> FEATURE:
<223> OTHER INFORMATION: Synthetic oligonucleotide (R316)

<400> SEQUENCE: 21
aaaaaacctc tttcaccaca aaccaagtac aaagcttc                            38

<210> SEQ ID NO 22
<211> LENGTH: 36
<212> TYPE: DNA
<213> ORGANISM: Artificial Sequence
<220> FEATURE:
<223> OTHER INFORMATION: Synthetic oligonucleotide (F335)

<400> SEQUENCE: 22
gtggtgaaag aggtttttc tacactccaa aggctg                               36

<210> SEQ ID NO 23
<211> LENGTH: 36
<212> TYPE: DNA
<213> ORGANISM: Artificial Sequence
<220> FEATURE:
<223> OTHER INFORMATION: Synthetic oligonucleotide (R354)

<400> SEQUENCE: 23
tgttcaacaa taccttggc agcctttgga gtgtag                               36

<210> SEQ ID NO 24
<211> LENGTH: 38
<212> TYPE: DNA
<213> ORGANISM: Artificial Sequence
<220> FEATURE:
<223> OTHER INFORMATION: Synthetic oligonucleotide (F371)

<400> SEQUENCE: 24
ccaagggtat tgttgaacaa tgttgcactt caatctgt                            38

<210> SEQ ID NO 25
<211> LENGTH: 39
<212> TYPE: DNA
<213> ORGANISM: Artificial Sequence
<220> FEATURE:
<223> OTHER INFORMATION: Synthetic oligonucleotide (R390)

<400> SEQUENCE: 25
ttctccaatt ggtacaaaga acagattgaa gtgcaacat                           39

<210> SEQ ID NO 26
<211> LENGTH: 41
<212> TYPE: DNA
<213> ORGANISM: Artificial Sequence
<220> FEATURE:
<223> OTHER INFORMATION: Synthetic oligonucleotide (F409)

<400> SEQUENCE: 26
```

```
tctttgtacc aattggagaa ctactgtaac taatagggcg g                           41

<210> SEQ ID NO 27
<211> LENGTH: 46
<212> TYPE: DNA
<213> ORGANISM: Artificial Sequence
<220> FEATURE:
<223> OTHER INFORMATION: Synthetic oligonucleotide (R429)

<400> SEQUENCE: 27
gcaaatggca ttctgacatc cgcggccgcc ctattagtta cagtag                     46

<210> SEQ ID NO 28
<211> LENGTH: 25
<212> TYPE: DNA
<213> ORGANISM: Artificial Sequence
<220> FEATURE:
<223> OTHER INFORMATION: Synthetic oligonucleotide (R450)

<400> SEQUENCE: 28
ccgcggatgt cagaatgcca tttgc                                            25
```

POLYNUCLEOTIDE AND POLYPEPTIDE SEQUENCE AND METHODS THEREOF

TECHNICAL FIELD

Figure 1:
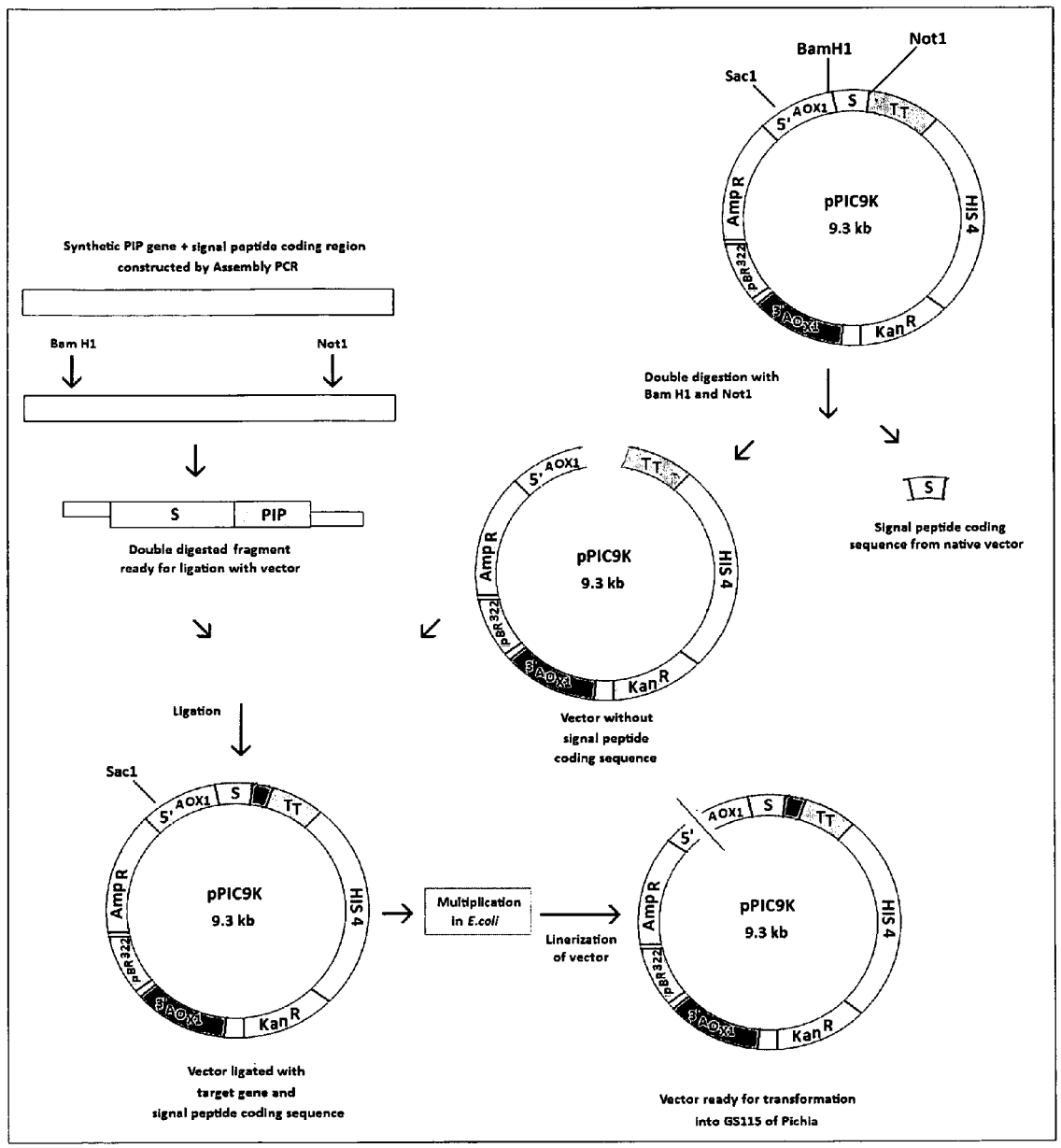

The present disclosure relates to a field of recombinant DNA therapeutics. It involves the bio-informatics design, synthesis of artificial gene for human insulin precursor including leader peptide coding sequence, cloning in an expression vector and expression in an organism, preferably *Pichia pastoris*. The present disclosure also relates to methods of downstream processing for obtaining protein precursor molecules and subsequent conversion of precursor molecules to functional proteins.

BACKGROUND OF THE DISCLOSURE

Human Insulin is a polypeptide hormone involved in regulation of glucose in blood and body fluids. Production deficiency leads to type 1 or type 2 diabetes. Type 1 is especially Insulin dependent diabetes. Earlier, Insulin used to be supplemented from animal sources (bovine and pig), which often results in undesirable allergic immune response or hypersensitive reaction on continual administration for longer periods. The next generation of Humanized Insulin was produced in *E. coli* by recombinant DNA technology and is being successfully used for the past several years. Although recombinant human Insulin is being expressed in different hosts through patented processes to meet the diabetes therapeutic requirements, the demand is growing and forcing the man kind to explore new and modified methods to produce commercially viable quantities.

Recombinant human Insulin currently available in the market is produced from at least three different expression systems i.e. *E. coli*, *Pichia pastoris* and *Hansenula polymorpha*. Over expression in *E. coli* results in proteins accumulating as insoluble inclusion bodies. Solubilization and refolding of the recombinant Insulin from the inclusion bodies requires use of chaotropic chemicals such as guanidine hydrochloride, urea, etc. and presence of traces of these chemicals in the final product even after extensive purification could be hazardous. Alternatively, proteins can be expressed in yeast system and secreted out into the medium at much higher levels in soluble form. However, levels of expression obtained in each yeast system differed from protein to protein for unknown reasons.

The two chains of Human Insulin are also being expressed separately using two different vectors and assembled together in-vitro after purification. Disulphide linkages between two chains is facilitated by chemical methods

STATEMENT OF THE DISCLOSURE

Accordingly, the present disclosure relates to a polynucleotide sequence as set forth in SEQ ID NO: 2; a polypeptide sequence as set forth in SEQ ID NO: 1; a method for obtaining recombinant insulin precursor molecule having polypeptide sequence as set forth in SEQ ID NO: 1, said method comprising steps of: a) synthesizing a polynucleotide sequence set forth in SEQ ID NO: 2 by combining 26 oligonucleotides of SEQ ID NOS: 3 to 28 by assembly PCR, and inserting the synthesized sequence in a vector, b) transforming a host cell with said vector followed by antibiotic screening host selection, and c) fermenting the selected transformed host cell and in-situ capturing of the insulin precursor molecule to obtain said precursor having polypeptide sequence as set forth in SEQ ID NO: 1; a method of downstream processing for in-situ capturing of protein precursor molecule during fermentation process, said method comprising steps of: a) simultaneous pumping of fermentation product obtained during fermentation into a hollow fibre harvesting system to obtain permeate and retentate, b) recycling of the retentate into the fermentor, and c) subjecting the permeate through ion-exchange chromatographic column followed by washing with TRIS elution buffer to obtain said protein precursor molecule; a method of downstream processing for in-situ conversion of protein precursor molecule into functional protein molecule, said method comprising step of: a) concentrating the precursor molecule through TFF Cassette and mixing the concentrate with organic solution to obtain retentate reaction mixture, b) subjecting the reaction mixture to incubation through TPCK trypsin immobilized column to obtain protein ester, and c) subjecting the ester to deblocking buffer followed by hydrophobic interaction chromatographic column to obtain said functional protein molecule; a method for obtaining recombinant insulin molecule from a precursor molecule having polypeptide sequence as set forth in SEQ ID NO: 1, said method comprising steps of: a) synthesizing a polynucleotide sequence set forth in SEQ ID NO: 2 by combining 26 oligonucleotides of SEQ ID NOS: 3 to 28 by assembly PCR, b) inserting the synthesized sequence in a vector and transforming a host cell with said vector followed by antibiotic screening host selection, c) fermenting the selected transformed host cell followed by downstream processing for in-situ capturing of the insulin precursor molecule, and d) in-situ conversion of insulin precursor molecule having polypeptide sequence as set forth in SEQ ID NO: 1 into said recombinant insulin molecule; a recombinant vector comprising the polynucleotide sequence set forth in SEQ ID NO: 2; and a recombinant host cell, transformed by introduction of a vector comprising polynucleotide sequence set forth in SEQ ID NO: 2;

BRIEF DESCRIPTION OF ACCOMPANYING FIGURES

FIG. 01: Flow chart of cloning process—construction of insert, preparation of vector for ligation, ligation of insert with vector, preparation of vector for *Pichia* transformation.

Figure 2:
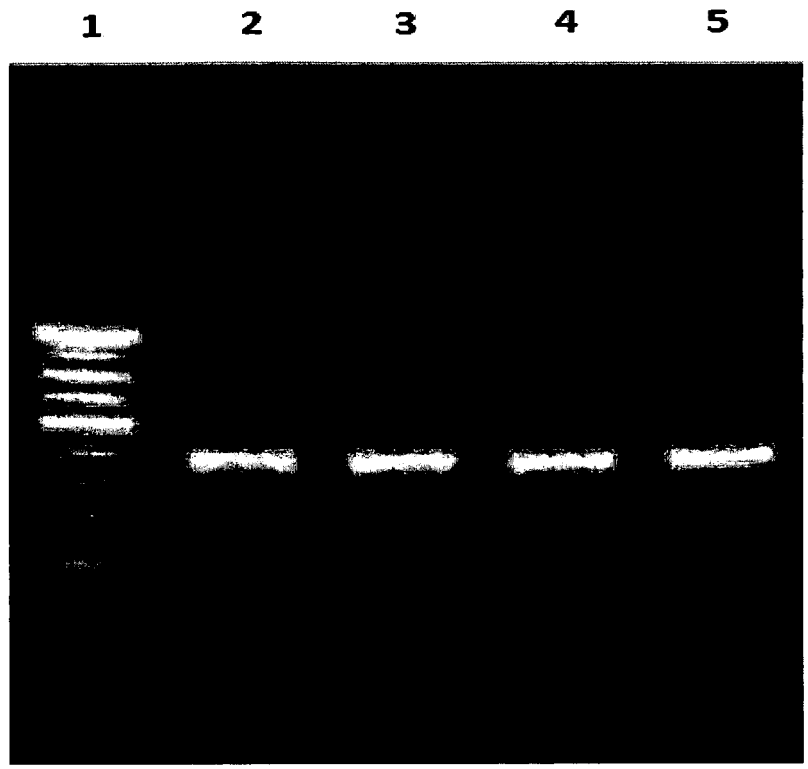

FIG. 02: Agarose gel image of gene construct from Oligos by Assembly PCR.
Lane 1: 100 base pair DNA ladder and Lanes 2-5: Assembled gene amplified (Amplicon size 640 by along with AOX1 region)

Figure 2A:
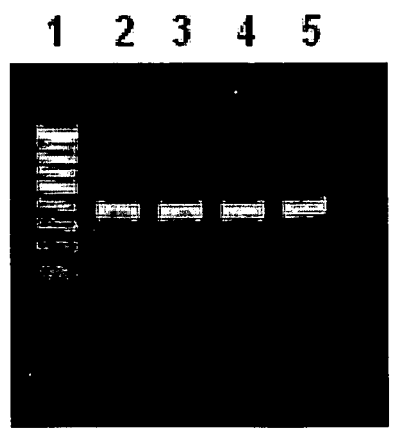
Figure 3:
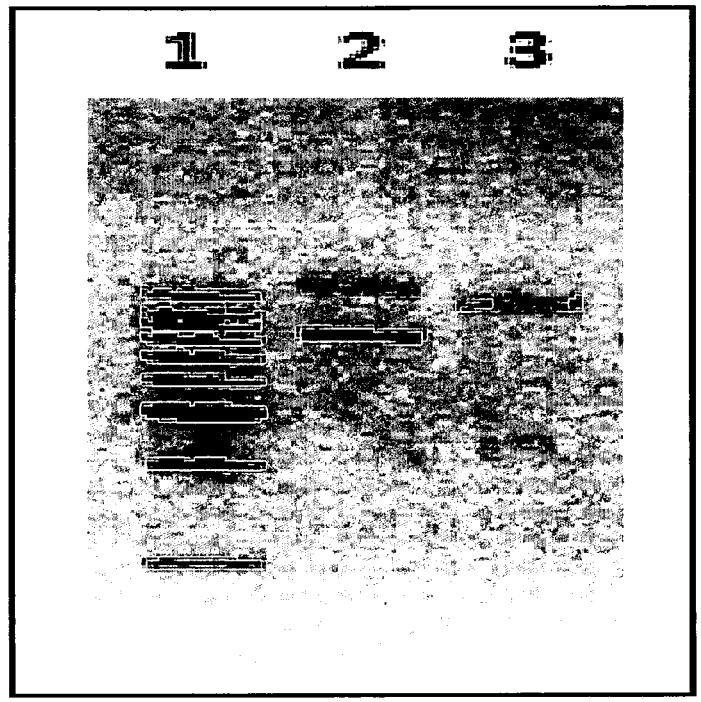
Figure 4:
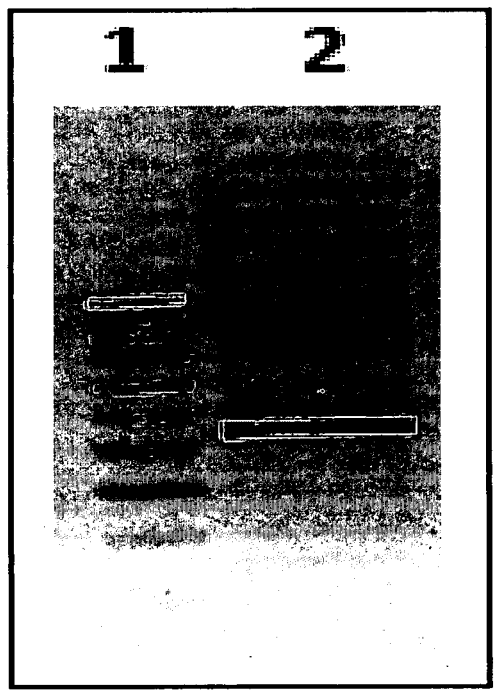

FIG. 2a: Gel Electrophoresis—The product of second PCR is checked on 1% agarose gel in TAE buffer
1% agarose gel casting
Loading—1.5 μl sucrose dye+5 μl-10 μl PCR product
Marker—100 bp marker 0.8-1.0 μl +2 μl milliQ+1.5 dye
PCR amplicon size is 483 and is seen on gel around 500 bp FIG. 03: Double enzyme digestion of pPIC9K vector with BamHl and Notl
Lane 1: 1 kb DNA ladder
Lane 2: pPIC9K before digestion
Lane 3: pPIC9K after digestion FIG. 04: Double enzyme digestion of target gene with BamHl and Notl
Lane 1: 100 bpb DNA ladder
Lane 2: gene double digest FIG. 05: Alignment of the "designed" polynucleotide (SEQ ID NO: 2) with the DNA sequencing profile.

Figures 5, 6:
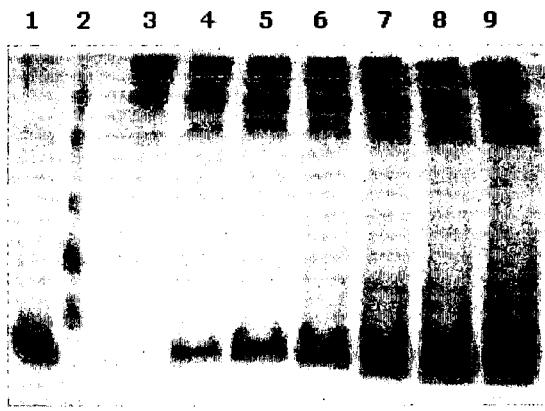

FIG. 06: SDS-PAGE (15%) image of fermentation samples during different stages of induction showing continuous increase of expression and secretion of Insulin precursor into the fermentation medium.

Lane 1: Standard PIP
Lane 2: Protein molecular weight marker;
Lane 3: Fermentation sample at 0 hour of induction;
Lane 4: Fermentation sample at 6 hour of induction;
Lane 5: Fermentation sample at 12 hour of induction;
Lane 6: Fermentation sample at 24 hour of induction;
Lane 7: Fermentation sample at 30 hour of induction; Lane
Lane 8: Fermentation sample at 36 hour of induction and
Lane 9: Fermentation sample at 42 hour of induction FIG. 07: HPLC profile of Fermentation samples at different periods of induction. [quantity of insulin precursor Vs Time course of fermentation induction phase].
There is a progressive increase in the quantity of precursor from time to time of induction period. The increase in quantity is correlated with size of peaks expressed as milli volts.

Figure 8:
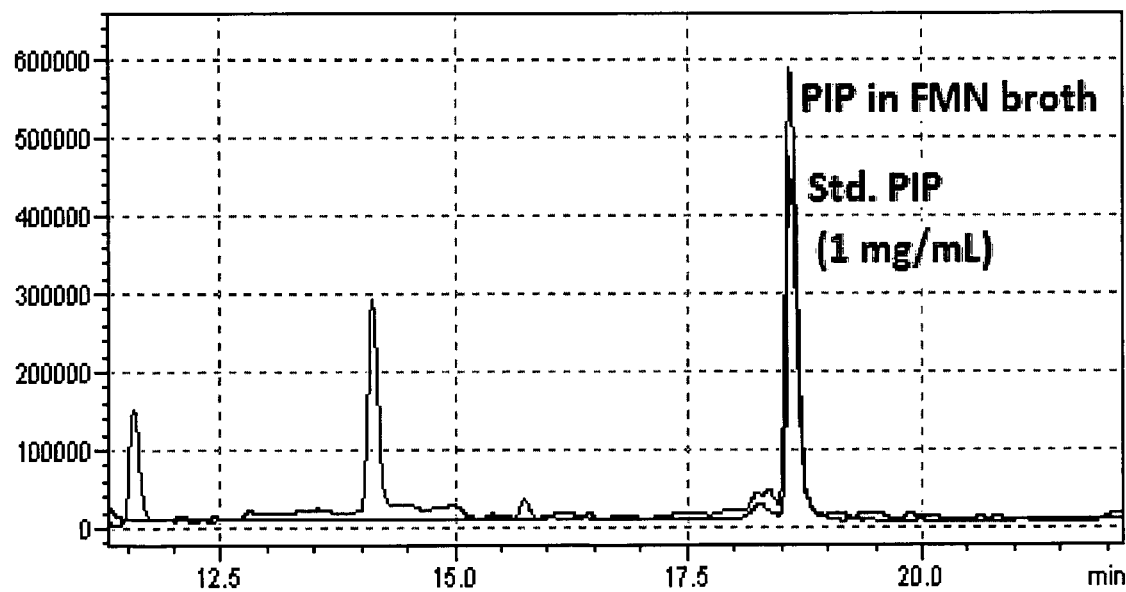

FIG. 08: Comparative HPLC profile of standard precursor and precursor in fermentation (final) sample, showing selective capturing of Insulin Precursor. The peak corresponding to standard obtained from protein concentration of 1 mg/mL. The peak corresponding to fermentation sample is obtained from 1:1 dilution of broth. 50% diluted FMN broth peak is more than that of standard precursor. It corresponds ≥2 g/lit.

Figure 9:
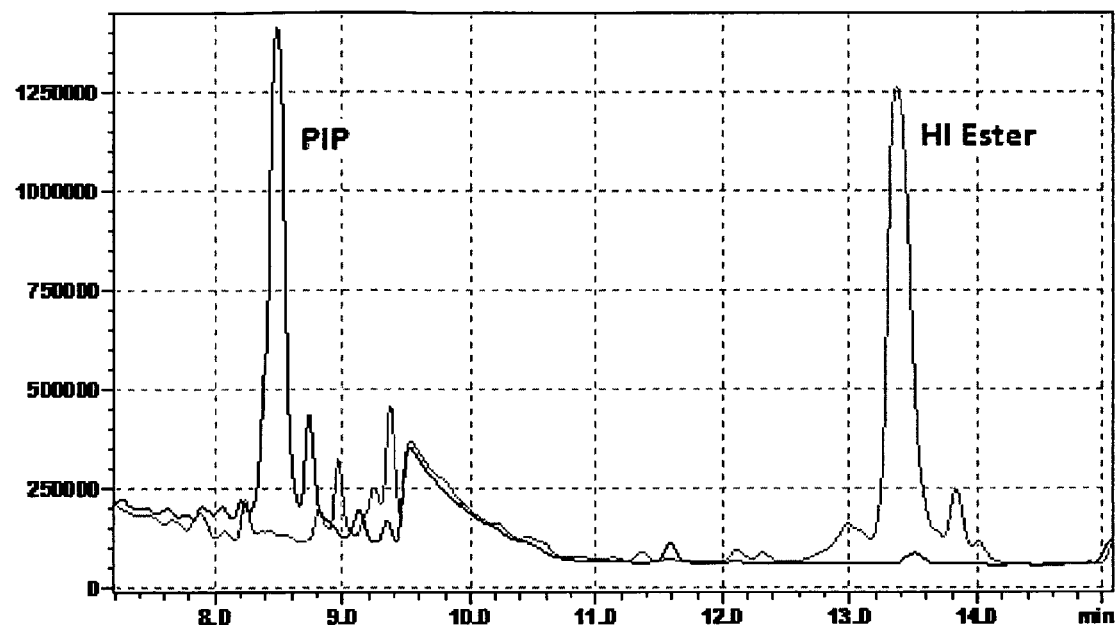

FIG. 09: HPLC profile of enzymatic conversion of Insulin Precursor (PIP) to Human Insulin butyl ester (Transpeptidation Product). Before Transpeptidation reaction, said PIP was loaded. After trypsin digestion and transpeptidation, the product (HI ester) is also loaded onto HPLC to confirm completion of the reaction. The mass balance is almost matched between precursor and its Transpeptidation product.

Figure 10:
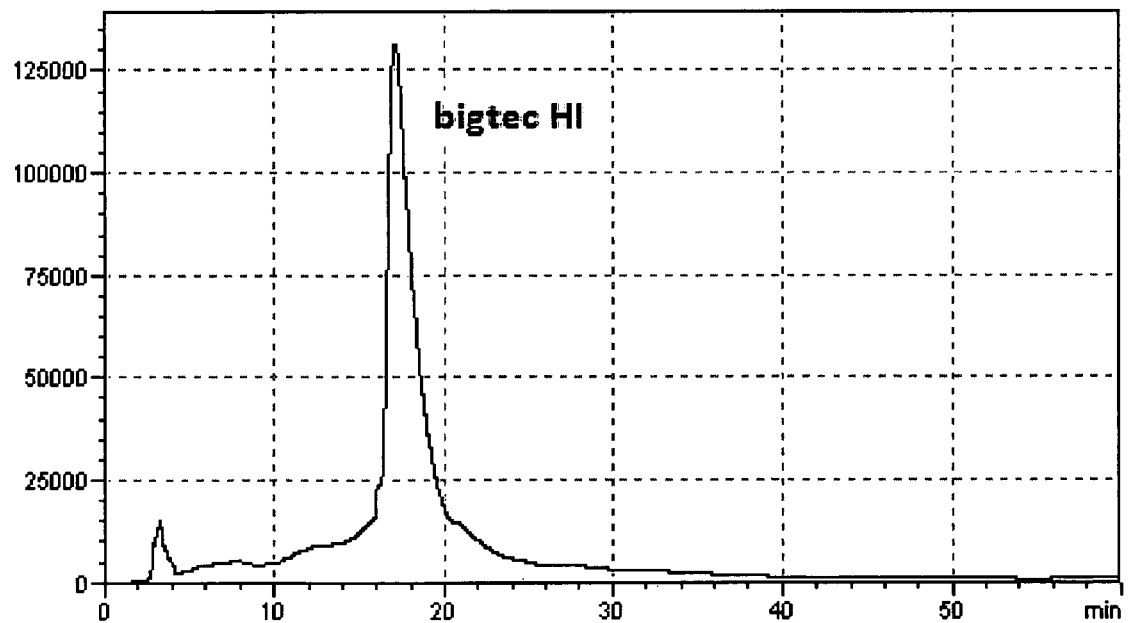

FIG. 10: The TP product is deblocked to obtain Human insulin and loaded onto HPLC to know the purity and profile. In terms of mass balance it is matching with PIP (precursor). Both PIP in FIG. 09 and HI in this figure are loaded at the same concentration (1 mg/mL). (Purified Human Insulin HPLC profile as per British Pharmacopeia 2007).

Figure 11:
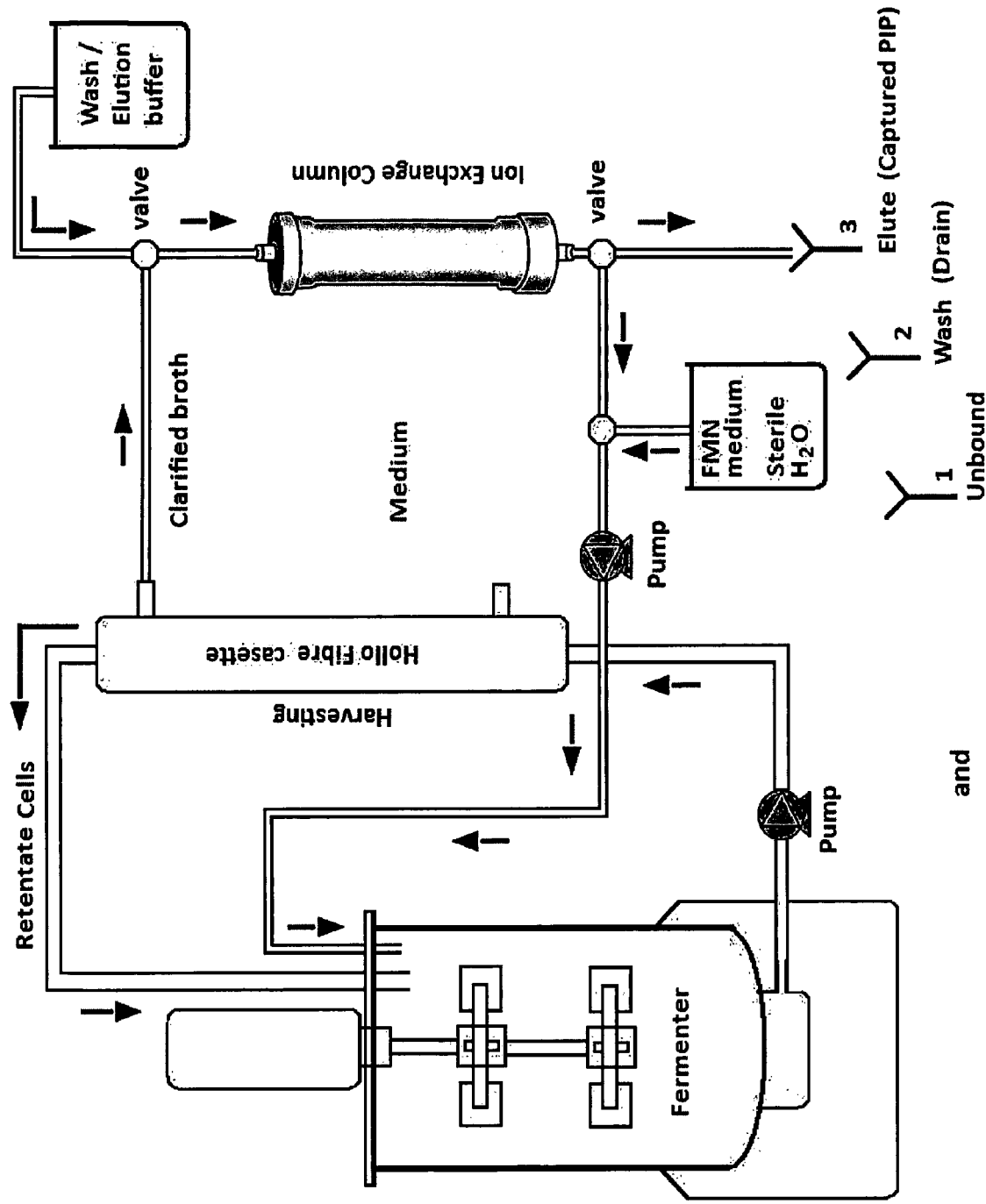

FIG. 11: Diagram showing the flow chart of fermentation, in-situ harvesting and clarification of fermentation broth by a hollow fibre harvesting system with 0.2 μM cassette. The cells retained after harvesting are directed back into fermenter along with fresh medium.

Figure 12:
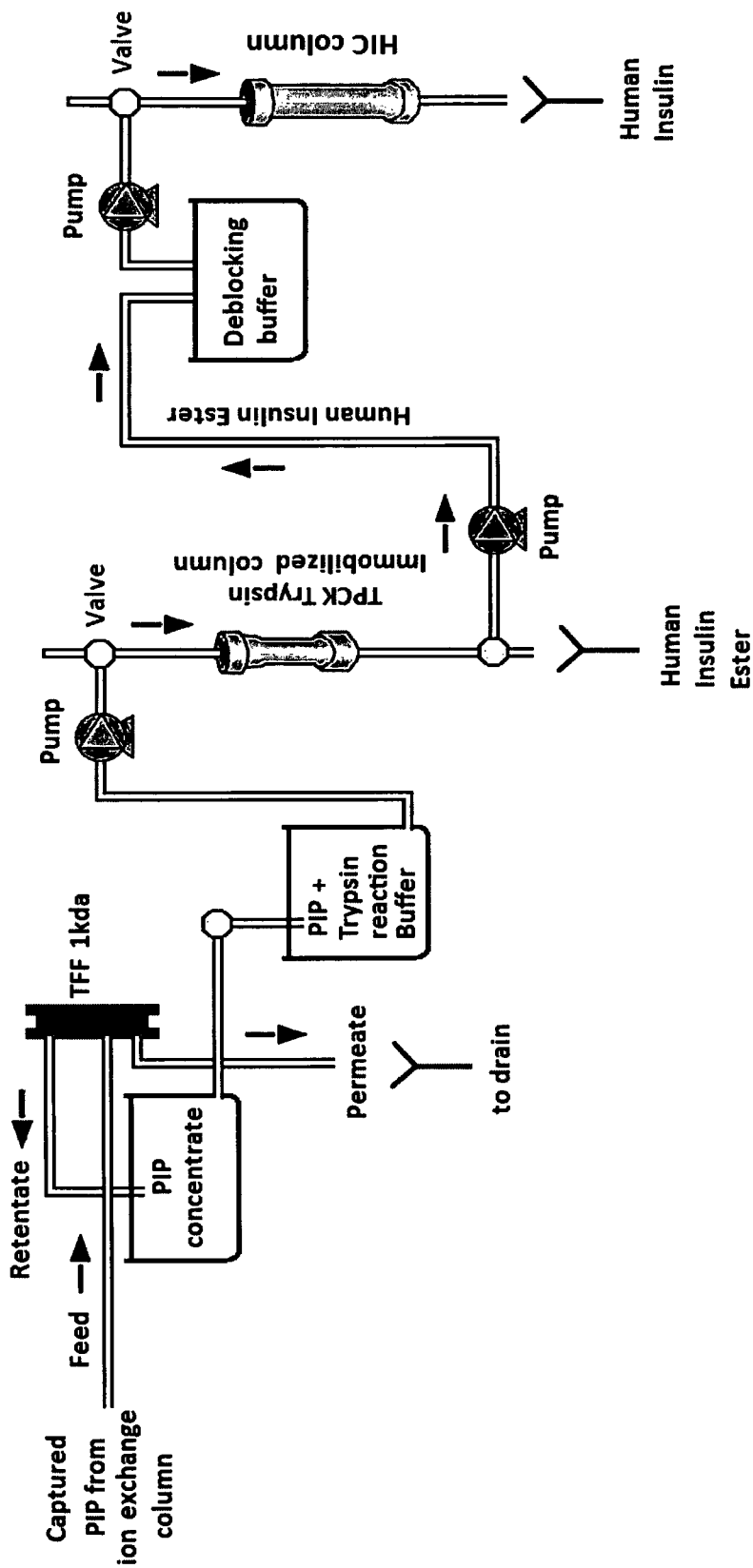

FIG. 12: Diagram shows the flowchart of concentration and in-situ capturing of human insulin precursor in cation exchange chromatography column followed by in-situ digestion and transeptidation in TPCK trypsin immobilized column for conversion into insulin butyl ester. Human insulin ester is deblocked and passed through HIC column to get purified human insulin.

Figure 13:
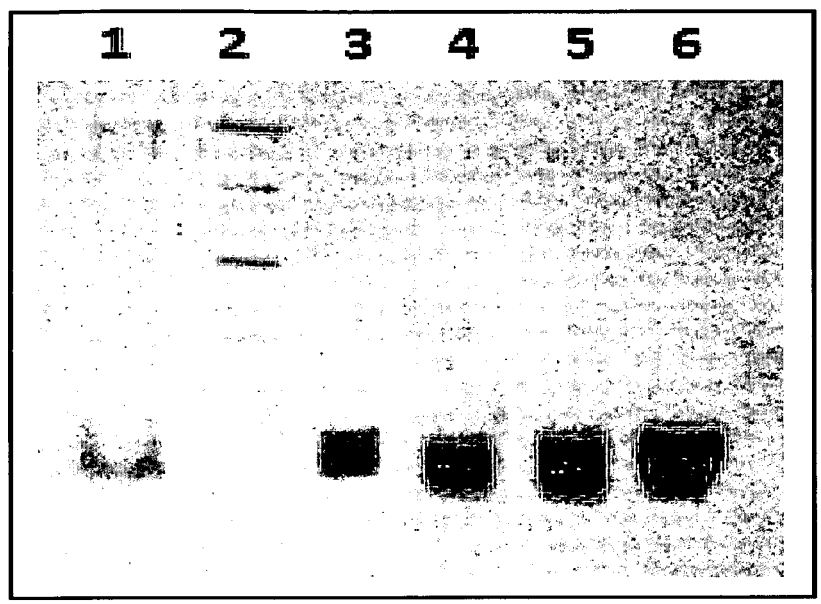

FIG. 13: SDS PAGE (15%) of purified Human Insulin and comparison with commercial formulation;
Lane 1: Insulin Precursor;
Lane 2: protein molecular weight marker;
Lane 3: Purified Insulin Precursor;
Lane 4: Human insulin after deblocking;
Lane 5: Human insulin after polishing and
Lane 6: Commercial recombinant Human Insulin (Huminsulin R)

Figure 14:
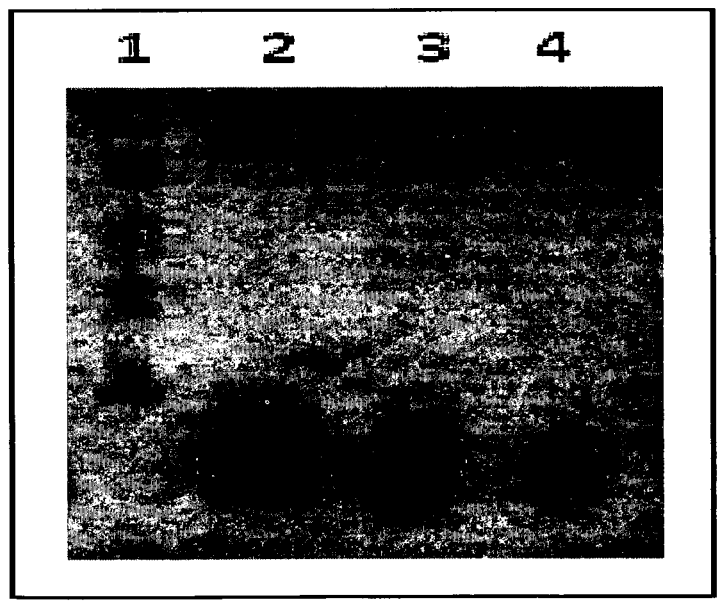
Figure 15:
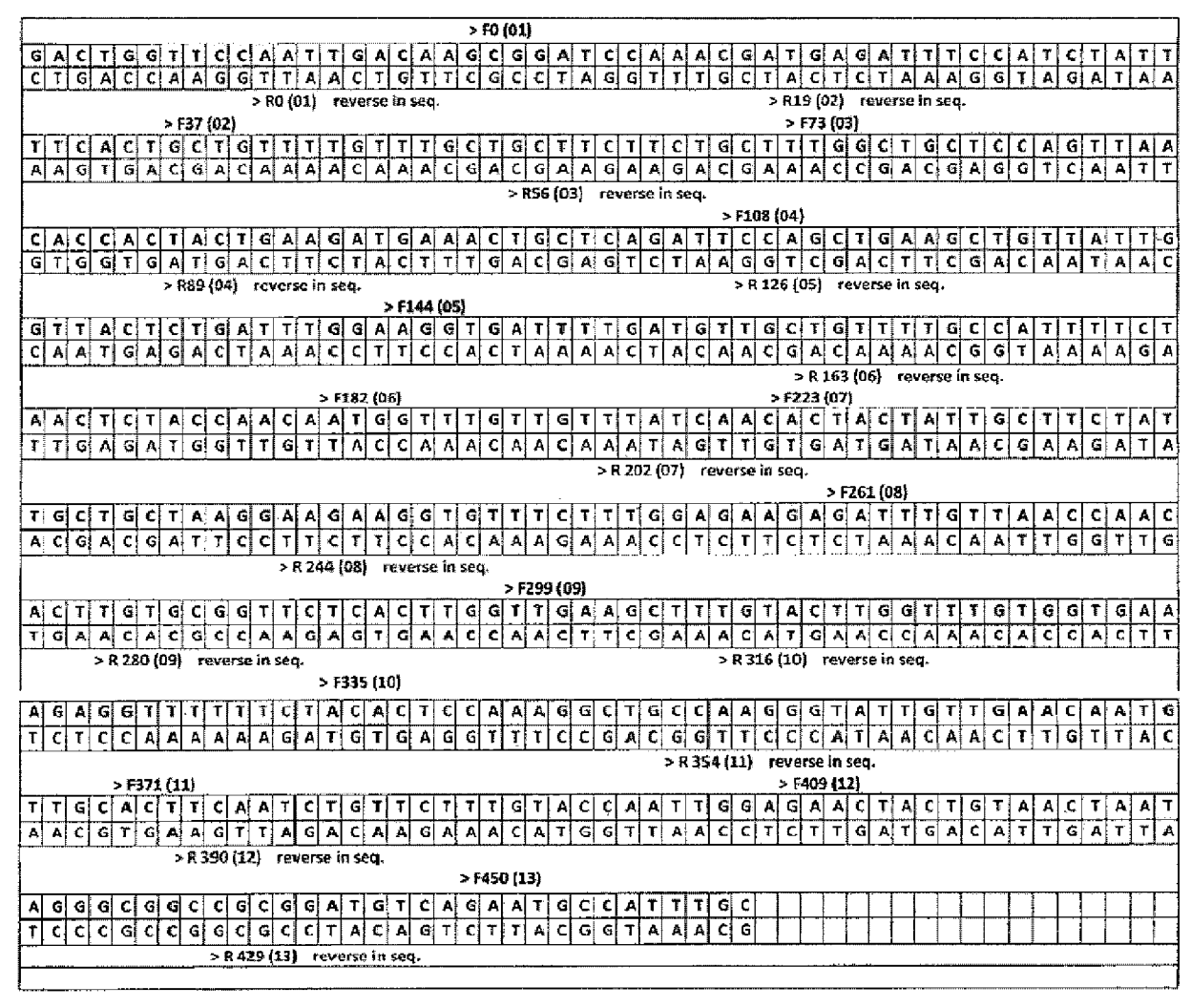

FIG. 14: Western Blot image of Insulin precursor and purified HI and commercial HI
Lane 1: Prestained protein marker
Lane 2: Insulin precursor captured from FMN broth
Lane 3: Purified bigtec human Insulin
Lane 4: Commercial human insulin FIG. 15: Product of the assembly PCR (that joined SEQ ID NOS: 3-28 to give SEQ ID NO 2).

DETAILED DESCRIPTION OF THE DISCLOSURE

The present disclosure relates to a polynucleotide sequence as set forth in SEQ ID NO: 2.

In an embodiment of the present disclosure, the polynucleotide encodes a fusion polypeptide comprising recombinant Human Insulin Precursor and signal peptide.

The present disclosure relates to a polypeptide sequence as set forth in SEQ ID NO: 1. In an embodiment of the present disclosure, the polypeptide is a fusion polypeptide comprising recombinant Human Insulin Precursor and signal peptide.

In another embodiment of the present disclosure, the polypeptide sequence corresponds to polynucleotide sequence set forth in SEQ ID NO: 2, wherein the polynucleotide is subjected to post-transcriptional modification and codon optimization to obtain corresponding polypeptide of SEQ ID NO: 1.

The present disclosure relates to a method for obtaining recombinant insulin precursor molecule having polypeptide sequence as set forth in SEQ ID NO: 1, said method comprising steps of:
a) synthesizing a polynucleotide sequence set forth in SEQ ID NO: 2 by combining 26 oligonucleotides of SEQ ID NOS: 3 to 28 by assembly PCR, and inserting the synthesized sequence in a vector,
b) transforming a host cell with said vector followed by antibiotic screening host selection, and
c) fermenting the selected transformed host cell and in-situ capturing of the insulin precursor molecule to obtain said precursor having polypeptide sequence as set forth in SEQ ID NO: 1.

In an embodiment of the present disclosure, the polypeptide is a fusion polypeptide comprising recombinant Human Insulin Precursor and signal peptide.

In another embodiment of the present disclosure, the synthesized polynucleotide and the vector are subjected to restriction enzyme digestion for insertion of the polynucleotide into the expression vector and wherein restriction enzymes are selected from a group comprising BamHI, NotI, SacI, BgIII and SacII or any combination thereof.

In yet another embodiment of the present disclosure, the vector is selected from a group comprising pPIC9K and pPICZα, preferably pPIC9K and wherein the host is selected from a group comprising *Pichia pastoris, Pichia methanolica; Pichia guilliermondii* and *Pichia caribbica*, preferably *Pichia pastoris*.

In still another embodiment of the present disclosure, the in-situ capturing of the precursor molecule is carried out by hollow fibre harvesting system and ion-exchange chromatographic column to obtain said precursor.

The present disclosure relates to a method of downstream processing for in-situ capturing of protein precursor molecule during fermentation process, said method comprising steps of:
a) simultaneous pumping of fermentation product obtained during fermentation into a hollow fibre harvesting system to obtain permeate and retentate,
b) recycling of the retentate into the fermentor, and
c) subjecting the permeate through ion-exchange chromatographic column followed by washing with TRIS elution buffer to obtain said protein precursor molecule.

In an embodiment of the present disclosure, the permeate comprise of clarified cell free broth and the retentate comprise of concentrated cells.

In another embodiment of the present disclosure, the wherein the retentate is recycled back to fermentor vessel along with fresh medium in the fermentor and the permeate is passed through the ion-exchange chromatographic column for capturing the protein precursor.

In yet another embodiment of the present disclosure, the protein precursor selectively binds to polymer matrix of the ion-exchange chromatographic column and is eluted with the elution buffer.

The present disclosure relates to a method of downstream processing for in-situ conversion of protein precursor molecule into functional protein molecule, said method comprising step of:
  a) concentrating the precursor molecule through TFF Cassette and mixing the concentrate with organic solution to obtain retentate reaction mixture,
  b) subjecting the reaction mixture to incubation through TPCK trypsin immobilized column to obtain protein ester, and
  c) subjecting the ester to deblocking buffer followed by hydrophobic interaction chromatographic column to obtain said functional protein molecule.

In an embodiment of the present disclosure, the precursor molecule is concentrated to a range of about 100 mg/ml to about 200 mg/ml.

In another embodiment of the present disclosure, the organic solution comprise of O-tert-Butyl-L-theronine tert-butyl ester acetate dissolved in 1:1 v/v dimethyl sulfoxide (DMSO):Methanol and the deblocking buffer comprise a combination of tryptophan and trifluoroacetic acid.

In another embodiment of the present disclosure, the TPCK column is equilibrated with a combination of $CaCl_2$ and Acetic acid and the hydrophobic interaction chromatographic column is equilibrated with a combination of Acetic acid and Ammonium sulphate.

In another embodiment of the present disclosure, time for the incubation ranges from about 1.5 hrs to about 3.5 hrs and temperature for the incubation ranges from about 15° C. to about 25° C.

The present disclosure relates to a method for obtaining recombinant insulin molecule from a precursor molecule having polypeptide sequence as set forth in SEQ ID NO: 1, said method comprising steps of:
  a) synthesizing a polynucleotide sequence set forth in SEQ ID NO: 2 by combining 26 oligonucleotides of SEQ ID NOS: 3 to 28 by assembly PCR,
  b) inserting the synthesized sequence in a vector and transforming a host cell with said vector followed by antibiotic screening host selection,
  c) fermenting the selected transformed host cell followed by downstream processing for in-situ capturing of the insulin precursor molecule, and
  d) in-situ conversion of insulin precursor molecule having polypeptide sequence as set forth in SEQ ID NO: 1 into said recombinant insulin molecule.

In an embodiment of the present disclosure, the polypeptide is a fusion polypeptide comprising recombinant Human Insulin Precursor and signal peptide.

In another embodiment of the present disclosure, the synthesized polynucleotide and the vector are subjected to restriction enzyme digestion for insertion of the polynucleotide into the expression vector and wherein the restriction enzymes are selected from a group comprising BamHI, NotI, SacI, BgIII and SacII or any combination thereof.

In yet another embodiment of the present disclosure, the vector is selected from a group comprising pPIC9K and pPICZα, preferably pPIC9K and wherein the host is selected from a group comprising *Pichia pastoris, Pichia methanolica, Pichia guilliermondii* and *Pichia caribbica*, preferably *Pichia pastoris*.

In still another embodiment of the present disclosure, the in-situ capturing of the precursor molecule is carried out by hollow fibre harvesting system and ion-exchange chromatographic column to obtain said precursor.

In still another embodiment of the present disclosure, the in-situ conversion of the precursor molecule is carried out by subjecting the precursor molecule to TFF Cassette and TPCK trypsin immobilized column to obtain protein ester.

In still another embodiment of the present disclosure, the protein ester is subjected to deblocking buffer followed by hydrophobic interaction chromatographic column to obtain said recombinant insulin molecule.

The present disclosure relates to a recombinant vector comprising polynucleotide sequence set forth in SEQ ID NO: 2.

In an embodiment of the present disclosure, the vector is selected from a group comprising pPIC9K and pPICZα, preferably pPIC9K.

The present disclosure relates to a recombinant host cell, transformed by introduction of a vector comprising polynucleotide sequence set forth in SEQ ID NO: 2.

In an embodiment of the present disclosure, the host is selected from a group comprising *Pichia pastoris, Pichia methanolica, Pichia guilliermondii* and *Pichia caribbica*, preferably *Pichia pastoris* and wherein the vector is selected from a group comprising pPIC9K and pPICZα, preferably pPIC9K.

The main object of the present disclosure is to de novo design and express the gene coding for "secretion signal and recombinant Insulin Precursor fusion protein" comprising the amino acid sequence as set forth in SEQ ID NO: 1.

The present disclosure relates to a method for obtaining recombinant human insulin, said method comprising the steps of:
  a) Designing and constructing an insulin precursor-signal peptide fusion protein coding gene;
  b) Ligating the precursor-signal peptide fusion protein coding gene to a vector;
  c) Obtaining multiple copies of the precursor-signal peptide fusion protein coding gene by transformation (electroporation) into a host.
  d) Fermentation of transformed host cell lines to obtain recombinant human insulin precursor; and
  e) Obtaining the recombinant human insulin by efficient downstream processing of the human insulin precursor.

In the present disclosure optimization of nucleotide sequence was done for enhanced expression and secretion of target protein into fermentation medium.

Optimization at multiple steps during clone construction, cloning, transformation, fermentation, downstream processing resulted in overall increase in yield, scalability and biological efficacy. Down-stream processing is improvised with, in-situ capturing and in-situ conversion of precursor to final product to minimize the processing time, cost, manpower and conserve reagents.

In another embodiment of the present disclosure, said SEQ ID No. 2 is obtained by multiple stages in-silico optimization of nucleotide sequence based on "Codon-Pair Frequency" of highly expressed proteins in *Pichia pastoris*. The sequence was further tuned to enhance protein synthesis by mRNA secondary structure prediction and removing high melting stem loop structures, which enables un-restricted ribosome movement and high speed protein synthesis.

Codon Pair Optimization

Codon optimisation is a method of gene optimisation, where in the synthetic gene sequence is modified to match the "codon usage pattern" for a particular organism. Here, for a particular amino acid sequence, select "most frequently used codons" (from a list of degenarate codons for an aminoacid), by that organism. So that the aminoacid sequence remains same but with a different DNA sequence, matched for that organism. How-ever this does not consider the fact that codons are read by ribosomes in "pairs", during protein synthesis. There are 2 codon binding site in ribosome, on adjescent places. Extensive analysis was done and a particular pattern was observed in which the "codon-pairs" are used by *pichia pastoris*. So the construct DNA sequence was modified to match to this "codon-pair usage frequency". This methodology is novel and never reported for gene expression optimisation. A proprietary in-house developed software was used for this excercise. By doing this gene optimisation (FIG. 15), it was found that the expression level could be increased by approx 30%.

In another embodiment of the present disclosure, the whole gene sequence i.e. Insulin Precursor and secretion signal was subjected to optimization together, as it is expressed as a single chain protein in the expression host.

In yet another embodiment of the present disclosure, said precursor is constructed with about 26 oligonucleotides coding for Insulin precursor-Signal peptide fusion protein.

In yet another embodiment of the present disclosure, said vector is selected from a group comprising pPIC9K and pPICZα, preferably pPIC9K In still another embodiment of the present disclosure, said cloning is carried out at downstream of AOX1 promoter in pPIC9K vector.

In still another embodiment of the present disclosure, said host is selected from a group comprising *Pichia pastoris, Pichia methanolica, Pichia guilliermondii* and *Pichia caribbica*, preferably *Pichia pastoris*.

In still another embodiment of the present disclosure, said cloning was carried out by simultaneous multiple gene insertions and direct selection using an antibiotic to get high copy number of gene into the host In still another embodiment of the present disclosure, said fermentation is carried out in a modified low salt minimal medium at optimal temperature range, aeration, cell densities and feeding, which enables high level expression and easy downstream processing.

In still another embodiment of the present disclosure, fermentation process and harvesting process are coupled. It involves a hollow fibre harvesting module is connected to fermenter for in-situ filtration of broth during harvesting. The culture from fermenter is pumped to a hollow fibre cassette to separate cell free broth from the cells. The cells after filtration are recycled back to fermenter vessel along with medium to maintain culture volume and promote normal growth of culture.

In still another embodiment of the present disclosure capturing of human insulin precursor is coupled with trypsin digestion and transpeptidation in an immobilized trypsin column. It involves binding of insulin precursor in cell free broth from hollow fibre filtration system to a chromatography column packed with high binding capacity synthetic resin. The unbound is again channeled back into fermenter along with fresh medium.

The bound protein is eluted and further channeled into a column packed with TPCK trypsin immobilized to matrix. On the way to Trypsin column the eluted precursor is mixed with necessary buffers and desired PH. The precursor is converted into insulin ester by tryptic digestion and transpeptidation in the column. Then the insulin ester is eluted from column and deblocked to convert into human insulin and lyophilized. Finally the human insulin is polished to highest purity by reverse phase chromatography.

In still another embodiment of the present disclosure, said fermentation medium has a pH ranging from about 4.0-5.0, preferably about 4.75 during initial phase of fermentation; about 4.0-5.0, preferably about 4.80 during glycerol phase and about 4.0-5.0, preferably about 4.95 during induction phase.

In still another embodiment of the present disclosure, said temperature at fermentation ranges from about 29-30° C., preferably about 30.0° C. for batch phase; about 29-30° C., preferably about 29.5° C. for glycerol fed batch; and about 27-29° C., preferably about 28.0° C. for induction phase with methanol.

In still another embodiment of the present disclosure, said aeration at fermentation ranges from about 0.5-1.5 VVM pure air, preferably 1VVM pure air for batch phase; about 0.5-1.5 VVM air:oxygen, preferably about 1.0 VVM air: oxygen (about 90:10) for glycerol batch; and about 1.5 VVM air:oxygen ratio begins at about 85:15 and ends at about 40:60 with an increment/decrement of about 5 at about every 5 hours for methanol batch (induction phase).

In still another embodiment of the present disclosure, during fermentation glycerol feeding is carried out to promote high cell density growth before induction and is continued until cell density ($OD_{600}$) reaches about 500. Then methanol is fed exponentially to promote increased expression of target protein.

In the present disclosure, a synthetic gene having modified nucleotide sequences and coding for a gene comprising the Mat-α secretion signal, spacer, and the insulin precursor was designed de novo. Extensive bioinformatics analysis was used to arrive at a novel coding sequence, based on nucleotide patterns from highly expressed proteins in *Pichia pastoris*. The synthetic gene (482 bp) was constructed by synthesizing 26 oligonucleotides and combining them by assembly PCR.

*Pichia* expression system is known for its very high levels of expression, using a methanol inducible promoter. Proteins can be expressed as secretory proteins and therefore purification of the same becomes simple. The doubling time of the strain, ease of handling, minimal growth requirements, availability of convenient vectors, host systems and selection methodologies make *Pichia pastoris* an ideal and attractive system for study. High cell densities are achievable in minimal mineral media and the ease of induced expression of proteins adds to the convenience of using this system for recombinant protein expression.

The insulin precursor fusion protein gene obtained by assembly PCR was confirmed by DNA sequencing (FIG. 05) and was cloned into *Pichia pastoris* expression vector pPIC9K. The vector after linearization transformed into GS115 strain of *Pichia* by electroporation. The expression cassette was integrated into the *Pichia* host system by homologous recombination. Clones harboring high copy number inserts were picked by antibiotic screening. Clones showing maximum resistance to the antibiotic genticin (G418) were picked and screened for their ability to express and secrete the Insulin precursor into the culture medium. Promising clones were further evaluated by 7 liter capacity fermenter. The fermentation yield of insulin precursor is around 1.5 gm/litre. This can be further increased through additional optimization of the process.

The secreted insulin precursor was captured from the broth, purified and enzymatically modified to obtain Human Insulin. Biological activity of the final product in terms of regulating blood glucose has been established in mice and rats and found to be comparable with commercially available therapeutic recombinant Human Insulin formulations.

Thus, the process has been optimized at multiple steps, which has cumulative effects and resulted in increased yields. To name some of the major parameters optimized in this system, the "codon-pair sequence" of the entire coding region, stability of mRNA, multiple copy insertions, optimized media components and growth and induction parameters.

Integration of the expression cassette into the host genome ensures performance and stability of the recombinant strain after repeated sub-culturing. The possibility of multi-copy gene expression in the *Pichia* system makes it feasible to exploit the expression, folding and secretory capacities of the cells to the maximum. Expression of Human Insulin as a single chain protein enables proper disulphide bridge formation resulting in proper folding leading to a molecule that is biologically active. Further, the process of the present disclosure in which in-vitro processing and use of hazardous chemicals are kept to a minimum is ideally suited for scale-up and commercial production of recombinant Human Insulin. The fermentation yields are significantly better than reported literature and unreported market figures.

In still another embodiment of the present disclosure, fermentation yields are high.

In still another embodiment of the present disclosure, use of high efficiency synthetic polymeric resins for capturing and purification process resulted in enhanced recovery and purity with minimal unit operations, as depicted in examples given below. Use of synthetic resins enhanced the robustness of the process, stringent sanitation protocols and ease of scale-up & overall techno-economic feasibility of the process.

The disclosure is further elaborated with the help of following examples. However, these examples should not be construed to limit the scope of disclosure.

EXAMPLES

Example 1

Gene Construction and Clone Generation

26 Oligonucleotides [as given in SEQ 3] coding for the fusion protein "Mat-α-Insulin Precursor" fusion protein were designed and custom synthesized. These oligonucleotides were assembled by assembly PCR. The PCR product is double digested with restriction enzymes BamHI and NotI (FIG. 04) and ligated into similarly processed vector pPIC9K (FIG. 03) using T4 DNA ligase.

Assembly PCR

Master stocks of oligos resuspended in water and stored in original vials of Bioserve and kept in −20° C. Resuspension of oligos result in 100 pm/μl concentration of each oligo (1 μM=1 p mole/μl). Assembly PCR require 0.1 μM concentration of each oligo. 10 μl of each oligo is diluted to 200 μl (20 times) to give 5 μM solution. 1 μl of each diluted oligo is added to PCR master mix before assembly PCR.

TABLE 1

Reaction Mix; using Phusion High Fidelity DNA Polymerase (NEB) Kit

PCR MIX (50 μl)

| | |
|---|---|
| 5X rxn buffer (Hi Fidelity) | 10.0 μl |
| 10 mM dNTPs | 1.0 μl |
| Oligos | 26 μl |
| Taq | 0.5 μl (1 unit/μl) |
| MilliQ | 12.5 μl |
| Total volume | 50 μl |

TABLE 2

PCR Program for 1st Assembly PCR

PCR MIX (50 μl)

| | | | | |
|---|---|---|---|---|
| Step 1 | Initial denaturation | 98° C. | 30 sec | 1 cycle |
| Step 2 | Denaturation | 98° C. | 10 sec | 30 cycles |
| Step 3 | Annealing | 57° C. | 30 sec | |
| Step 4 | Extension | 72° C. | 30 sec | |
| Repeat 2, 3 & 4 | 30 times | | | |
| Step 5 | Final extension | 72° C. | 7 min | 1 cycle |
| Step 6 | Final Hold | 4° C. | α | |

The product of assembly PCR is used as template for $2^{nd}$ PCR. Product quantity is not increased in exponential way, hence it is not checked on gel electrophoresis. The product from assembly PCR is directly used as template for second PCR where the assembled gene is amplified by using AOX1 primers.

TABLE 3

Reaction Mix for amplification of Clone ($2^{nd}$ PCR)

PCR MIX (NEB) (20 μl)

| | |
|---|---|
| 5X rxn buffer (Hi Fidelity) | 4.0 μl |
| 10 mM dNTP mix | 0.4 μl |
| AOX1 Primer F (100 μM) | 0.2 μl |
| AOX1 Primer R (100 μM) | 0.2 μl |
| Template (Assembly PCR mix) | 1.2 μl |
| Phusion Taq (NEB) | 0.2 μl |
| MilliQ | 13.8 μl |
| Total volume | 20 μl |

TABLE 4

PCR Program for $2^{nd}$ PCR

PCR MIX (50 μl)

| | | | | |
|---|---|---|---|---|
| Step 1 | Initial denaturation | 95° C. | 30 sec | 1 cycle |
| Step 2 | Denaturation | 98° C. | 10 sec | 30 cycles |
| Step 3 | Annealing | 57° C. | 30 sec | |
| Step 4 | Extension | 72° C. | 30 sec | |
| Repeat 2, 3 & 4 | 30 times | | | |
| Step 5 | Final extension | 72° C | 7 min | 1 cycle |
| Step 6 | Final Hold | 4° C. | α | |

Resultant Sequence

Amplicon obtained from second PCR and size of the amplicon is matching with the size ~500 bp (482 bp). The product of second PCR is extracted from agarose gel for sequencing The ligation mix i.e. pPIC9K vector containing the ligated gene of interest (insulin precursor+mat-α secretion signal) is used for transformation into chemically competent TOP 10 *E. coli* strain (FIG. 01). $CaCl_2$ was used for competent cell preparation. Transformation was done by heat shock method. Transformation mix was plated on LB medium containing Ampicillin in order to select transformed colonies. Colonies were obtained after incubation of plates at 37° C. for 12-14 h. Glycerol stocks of transformed cells were prepared and stored at −70° C. Plasmid from *E. coli* is prepared by the protocol from Promega Kit (Wizard plus SV minipreps DNA purification system). Recombinant pPIC9K plasmid vector is linearized with restriction enzymes SacI/BglII/salI, purified, quantified and used for transformation into *Pichia pastoris*. Approximately 10 µg of the linearized plasmid DNA with insert were used for electroporation of electrocompetent host cells. The specifications used for electroporation are 760 Volts/5 milli seconds in 2 mm cuvette.

The transformation mixture was incubated in 1 M sorbitol for 30 min for cells to recover and further incubated in liquid regeneration media for 4 hours at 30° C. with shaking. Cells were then plated on to minimal media lacking histidine and containing antibiotic G418. The $His^+$ colonies that grew on these plates were screened by PCR by using AOX1 primers (FIG. 02) PCR positive cell lines are plated on fresh RD medium plates for further screening of high copy number lines.

Clones containing multiple copies of the gene inserted into the genome were further screened using higher concentrations of antibiotic G418. Colonies resistant to more than 4 mg G418 are considered to contain more than twelve copies of the gene. Such colonies were selected, grown on YPD medium and maintained as glycerol stock at −70° C.

Example 2

Expression Screening

Transformed colonies growing on RD plates with 4 mg G418 were screened for expression by shake flask cultures according to the Invitrogen's *Pichia* expression protocols. More than 100 such colonies were screened to identify few promising clones.

Each colony to be screened was grown in 5 ml YPD in a culture tube by incubating at 30° C./230 rpm/24 hrs. The seed (1 ml) is inoculated to 50 ml BMG (buffered minimum glycerol medium) in 250 ml Erlenmeyer flask and incubated at 30° C./220 rpm/24 hrs. Cells were harvested by centrifuging at 2000 g/5 minutes at room temperature. Supernatant was decanted and the cell pellet was resuspended in 25 ml BMM (buffered minimum methanol medium) in 150 ml baffled flasks and then allowed to grow at 30° C./200 rpm for 3 days. The culture was induced with methanol to a final concentration of 1.0% at every 24 hrs. Samples were taken at 24 hr intervals and analyzed by HPLC and SDS-PAGE.

Colonies showing good expression were made into glycerol stocks for further evaluation at fermentation level.

Example 3

High Cell Density Fermentation in Low Salt Minimal Media [LSMM]

Fermentation was carried in in-situ autoclavable automated vessel (BioFlo 415, NBS) of 7 litre capacity. All parameters like agitation, gas flow rates, feeding, pH adjustments, antifoam were controlled by PID controller.

The fermentation medium used is a Low Salt Minimal Medium (LSMM) supplemented with trace metal salts solution (PTM4) and Biotin, as follows:
Phosphoric acid=26.7 ml
$CaSO_4.2H_2O$=0.465 gm
$K_2SO_4$=9.1 gm
$MgSO_4.7H_2O$=7.45 gm
KOH=4.13 gm
Glycerol=50 ml
[All quantities per Liter of medium]

To promote rapid growth and high cell density yield in fermenter, glycerol stock is inoculated and grown in YPD medium by shake flask culture for 18-20 hrs at 220 rpm/30° C. till $OD_{600}$ reaches 10-12. The first seed is again inoculated onto YPG medium and grown at above mentioned conditions. When culture reached log phase (around 20 hrs) with $OD_{600}$ around 25-30, the cells are harvested at 1500 g/5 min and suspended in autoclaved milliQ water. Then cells are inoculated into basal salt medium in fermenter up to $OD_{600}$ of 5.0.

Batch phase: The fermenter medium pH adjusted to 4.75 before inoculation to avoid precipitation of medium if any. Dissolved oxygen (DO) probe is also calibrated before inoculation. Trace metal solution of 8% added to the vessel before and after inoculation at fixed intervals. Temperature of the culture is maintained at 30° C. Vessel aeration was maintained as 1.0 VVM pure air. Initial batch phase last for 18 hrs until $OD_{600}$ reaches 120-150 with an indication of DO shoot up.

Glycerol fed batch: The glycerol fed batch started with feeding of 50% glycerol containing 12% trace metal solution on exponential feed rate to achieve high cell density before induction. Temperature and pH were maintained at 29.5° C. and 4.80. Vessel aeration was maintained as 1.0 VVM air and oxygen in a ratio of 9:1.

Figure 7:
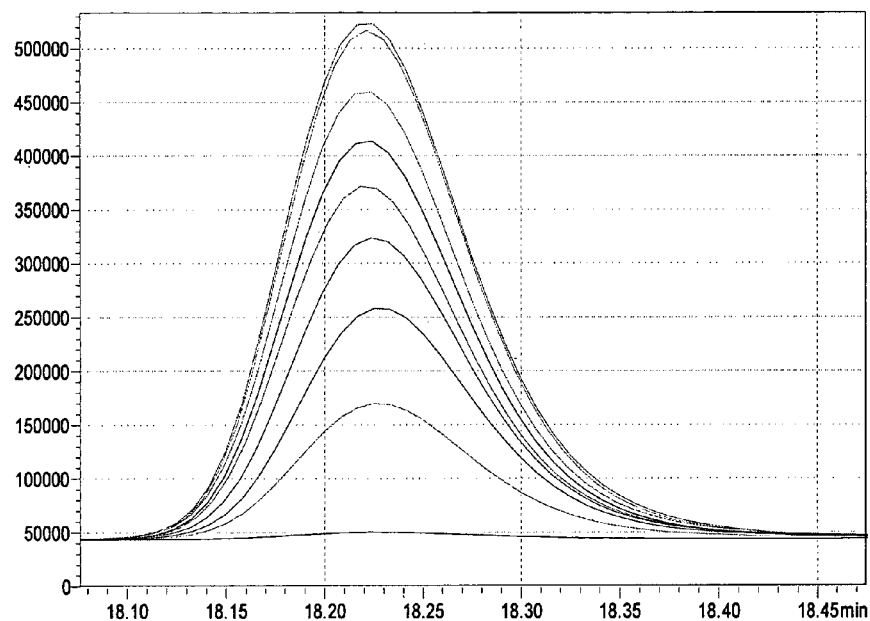

Methanol batch: Induction of Insulin Precursor (IP) was started by feeding 100% methanol containing 12% PTM4 trace metal solution. Initial methanol feed was given as spikes until culture gets adapted, subsequently switched on to exponential feed. The DO spike method was used to determine ramp of methanol feed. Methanol feed for $Mut^+$ and $Mut^s$ clones were based on Stratton et al., (*Pichia* protocols, Methods in Molecular Biology, Vol. 103). Residual methanol in the vessel is continuously monitored using an in-house designed methanol probe and sensor connected to the vessel. Consumption of methanol signals increase in vessel temperature which is maintained at 28.5° C. through out methanol fed batch. Medium pH was maintained at 4.95. Vessel aeration was maintained as 1.5 VVM due to high density with air and oxygen in a ratio begins at 85:15 and ends at 40:60 with an increment/decrement of 5 at every 5 hrs. During induction phase samples were analyzed at 6-hours interval to check growth, induction and contamination if any. Induced protein secreted into broth is analyzed by HPLC using 0.1% TFA/Acetonitrile solvents in C18 column. HPLC samples at 6 hour intervals showed progressive increase in protein level (FIG. 07). Fermentation samples were also analyzed by electrophoresis (SDS-PAGE) to assess the expression of insulin precursor and its increase with induction time (FIG. 06).

Fermentation samples during induction phase are periodically checked to know any protease activity by azocasein assay. Fermentation conditions were optimized for high level expression of insulin precursor which is more than 65% of total proteins present in the final sample. Results showed that the total protein present in the final sample is ranging from 2.3 g/L with insulin precursor being 1.5 g/L.

Example 4

Harvesting of Culture and In-Situ Capturing Insulin Precursor

When the induced culture is more than 36 hrs old, it is pumped from fermenter into hollow fiber harvesting system with 0.2μ cartridge via a peristaltic pump. The permeate contains clarified cell free broth and retentate contains concentrated cells. The retentate with cells is recycled back to fermenter vessel along with fresh medium to maintain normal growth and volume (FIG. 11).

The permeate containing clarified cell free broth is passed through column packed with strong cation exchanger resin, SP sepharose (methacrylic polymer with sulphopropyl functional derivatization—GigaCap S 650, Toyopearl) at pH 3.0. for protein capturing.

The column after protein binding is washed with 2 column volumes of pH 3.0 Tris buffer. The Insulin precursor selectively binds to the polymer matrix and is eluted with Tris buffer at pH 8.0. The chromatographic purity of insulin precursor is around 75% as checked on HPLC (FIG. 08) and step yield is around 90% w/w.

Example 5

In-Situ Conversion of Insulin Precursor to Human Insulin

The PIP obtained in Example 4 is converted to Human Insulin via trypsin mediated digestion and transpeptidation followed by deblocking. Insulin precursor eluted from ion exchange column is passed through 1 kda MWCO TFF cassette and concentrated to 100-200 mg/ml and its pH is adjusted to 7.3 with 1 N HCl. The concentrated PIP is mixed with O-tert-Butyl-L-theronine tert-butyl ester acetate dissolved in 1:1 v/v dimethyl sulfoxide (DMSO):Methanol. The reaction mixture is passed through TPCK-treated trypsin immobilized column (25 ml XK column with cooling jacket) equilibrated with 50 mM $CaCl_2$ and 0.5% acetic acid. When reaction mixture is completely loaded into the column, the column is closed for 2-3 hrs to permit incubation of reaction contents and column temperature is maintained at 20° C. Then the insulin precursor converted to Insulin butyl ester is eluted and checked by HPLC (FIG. 09).

After the completion of reaction in-situ, the elute from TPCK trypsin column is mixed with deblocking buffer i.e. 0.1% tryptophan in trifluoroacetic acid (TFA), incubated for 20 min at room temperature and passed into into hydrophobic interaction chromatography column (PPG 650 M Toyopearl) which is equilibrated with 100 mM Acetic acid having 0.8 M Ammonium sulphate for binding. The column is then washed with 100 mM Acetic acid with 0.4 M Ammonium sulphate, for 2 column volumes. Finally the bound Insulin was eluted with 100 mM acetic acid and lyophilized.

Step yield=75%
Chromatographic purity=85%

Example 6

Final Polishing of Human Insulin

Human Insulin obtained in example 5 is further purified from small molecular weight impurities and salts by size exclusion chromatography column packed with sepahdex G25 matrix and checked by HPLC and lyophilized to powder form.

Step yield=85%
Chromatographic purity=98.5%

The purified Human Insulin meets the quality norms as per monograph of recombinant Human Insulin under British Pharmacopoeia 2007, by HPLC analysis (FIG. 10) SDS PAGE (15%) (FIG. 13) and western blot (FIG. 14) of purified human insulin and comparison with commercial formulation is provided and.

---

We claim:

1. An isolated nucleic acid comprising the polynucleotide sequence as set forth in SEQ ID NO: 2.

2. The nucleic acid as claimed in claim 1, wherein the polynucleotide encodes a fusion polypeptide comprising recombinant human insulin precursor and a signal peptide.

3. A method for obtaining a recombinant insulin precursor molecule having the polypeptide sequence as set forth in SEQ ID NO: 1, said method comprising steps of:
   a) synthesizing the polynucleotide sequence set forth in SEQ ID NO: 2 by combining 26 oligonucleotides of SEQ ID NOS: 3 to 28 by assembly PCR, and inserting the synthesized polynucleotide sequence in a vector,
   b) transforming a host cell with said vector followed by antibiotic screening host selection, and
   c) fermenting the selected transformed host cell and in-situ capturing of the insulin precursor molecule to obtain said precursor having the polypeptide sequence as set forth in SEQ ID NO: 1.

4. The method as claimed in claim 3, wherein the polypeptide is a fusion polypeptide comprising recombinant human insulin precursor and a signal peptide.

5. The method as claimed in claim 3, wherein the synthesized polynucleotide and the vector are subjected to restriction enzyme digestion for insertion of the polynucleotide into the expression vector and wherein restriction enzymes are selected from a group comprising BamHI, NotI, SacI, BglII and SacII or any combination thereof.

6. The method as claimed in claim 3, wherein the vector is selected from a group comprising pPIC9K and pPICZα, preferably pPIC9K and wherein the host is selected from a group comprising *Pichia pastoris, Pichia methanolica, Pichia guilliermondii* and *Pichia caribbica*, preferably *Pichia pastoris*.

7. The method as claimed in claim 3, wherein the in-situ capturing of the precursor molecule is carried out by a hollow fibre harvesting and an ion-exchange chromatographic column to obtain said precursor.

8. A method for obtaining a recombinant insulin molecule from a precursor molecule having the polypeptide sequence as set forth in SEQ ID NO: 1, said method comprising steps of:
   a) synthesizing the polynucleotide sequence set forth in SEQ ID NO: 2 by combining 26 oligonucleotides of SEQ ID NOS: 3 to 28 by assembly PCR,
   b) inserting the synthesized polynucleotide sequence in a vector and transforming a host cell with said vector followed by antibiotic screening host selection,
   c) fermenting the selected transformed host cell followed by downstream processing for in-situ capturing of the insulin precursor molecule, and
   d) in-situ conversion of the insulin precursor molecule having the polypeptide sequence as set forth in SEQ ID NO: 1 into said recombinant insulin molecule.

9. The method as claimed in claim 8, wherein the polypeptide is a fusion polypeptide comprising recombinant human insulin precursor and a signal peptide.

10. The method as claimed in claim 8, wherein the synthesized polynucleotide and the vector are subjected to restriction enzyme digestion for insertion of the polynucleotide into the expression vector and wherein the restriction enzymes are selected from a group comprising BamHI, NoII, SacI, BgIII and SacII or any combination thereof.

11. The method as claimed in claim 8, wherein the vector is selected from a group comprising pPIC9K and pPICZα, preferably pPIC9K and wherein the host is selected from a group comprising *Pichia pastoris, Pichia methanolica, Pichia guilliermondii* and *Pichia caribbica*, preferably *Pichia pastoris*.

12. The method as claimed in claim 8, wherein the in-situ capturing of the precursor molecule is carried out by a hollow fibre harvesting system and an ion-exchange chromatographic column to obtain said precursor.

13. The method as claimed in claim 8, wherein the in-situ conversion of the precursor molecule is carried out by subjecting the precursor molecule to tangential flow filtration (TFF) Cassette and L-1-tosylamide-2-phenylethyl chloromethyl ketone (TPCK) trypsin immobilized column to obtain protein ester.

14. The method as claimed in claim 13, wherein the protein ester is subjected to deblocking buffer followed by hydrophobic interaction chromatographic column to obtain said recombinant insulin molecule.

15. A recombinant vector comprising the polynucleotide sequence set forth in SEQ ID NO: 2.

16. The recombinant vector as claimed in 15, wherein the recombinant vector is selected from a group comprising pPIC9K and pPICZα, preferably pPIC9K.

17. A recombinant host cell, transformed by introduction of a vector comprising the polynucleotide sequence set forth in SEQ ID NO: 2.

18. The host cell as claimed in claim 17, wherein the host is selected from a group comprising *Pichia pastoris, Pichia methanolica, Pichia guilliermondii* and *Pichia caribbica*, preferably *Pichia pastoris* and wherein the vector is selected from a group comprising pPIC9K and pPICZα, preferably pPIC9K.

* * * * *